United States Patent [19]

Herman

[11] Patent Number: 4,686,854
[45] Date of Patent: Aug. 18, 1987

[54] PROCESS AND APPARATUS FOR MEASURING CORROSION RATE OF A HEAT TRANSFER SURFACE

[75] Inventor: Kark W. Herman, Somerset, N.J.

[73] Assignee: Drew Chemical Corporation, Boonton, N.J.

[21] Appl. No.: 274,880

[22] Filed: Jun. 18, 1981

[51] Int. Cl.⁴ ............................................. G01N 17/00
[52] U.S. Cl. .......................................... 73/86; 73/61.2
[58] Field of Search ...................... 73/61.2, 86; 422/53

[56] References Cited

U.S. PATENT DOCUMENTS

| | | | |
|---|---|---|---|
| 3,627,493 | 12/1971 | Manley | 73/86 |
| 3,772,918 | 11/1973 | Bowles | 73/86 |
| 4,339,945 | 7/1982 | Knudsen | 73/61.2 |
| 4,346,587 | 8/1982 | Brindak | 73/61.2 |

Primary Examiner—Stewart J. Levy
Attorney, Agent, or Firm—Louis E. Marn

[57] ABSTRACT

There is disclosed a novel fouling and corrosion test assembly including a metallic tube having a heating element embedded in a heat conductive material for controlled heat input and with a thermocouple to measure wall temperature of the tube, and a metallic sleeve disposed about a predetermined portion of the metallic tube whereby the fouling and corrosion test assembly is disposed within conduit and valve assemblies in fluid flow communication with a fluid to determine corrosion rate by weight loss of the metallic sleeve under controlled heat input, temperature conditions and fluid flow rates for a predetermined time period.

16 Claims, 4 Drawing Figures

PROCESS AND APPARATUS FOR MEASURING CORROSION RATE OF A HEAT TRANSFER SURFACE

FIELD OF THE INVENTION

This invention relates to a process and apparatus for measuring the rate of corrosion, and more particularly, to a novel process and apparatus for measuring the corrosion rate of a heat transfer surface.

BACKGROUND OF THE INVENTION

Currently, prior art techniques to measure corrosion include either non-heat transfer methods, such as strip type or circular specimens, nipples, or changes in resistance of a thin metal tape or wire; or by heat transfer methods utilizing either single or multiple tube test exchangers. For non-heat transfer methods true conditions do not exist whereas for heat transfer methods actual velocity effect and/or surface temperatures are rarely identical, let alone provide accurate weight measurements.

In copending applications U.S. Ser. Nos. 202,351 now U.S. Pat. No. 4,339,945 and 202,352 now U.S. Pat. No. 4,346,587, assigned to the same assignee as the present invention and incorporated herein by reference, there are disclosed processes and apparatus for testing fluids for fouling characteristic. Fouling is an extremely complex phenomenon. From a fundamental point of view, it may be characterized as a combined momentum, heat and mass transfer problem. In many instances, chemcial reaction kinetics is involved, as well as solubility characteristics of salts in water and corrosion technology. It has been stated that if the fouling tendency of a cooling water can be accurately predicted before a plant is designed and built, significant capital savings might be realized through more accurate heat exchanger specifications.

As part of the process and apparatus, there is provided a heat transfer test assembly including a heat member for controlled heat input and thermocouples to measure wall temperatures of the heating member to permit fouling determinations at varying flow rates with simultaneous monitoring and recording thereof together with data, such as corrosion, pH, conductivity and the like. Measurement of corrosion is effected by a corrolator wherein current flow through an electrically conductive liquid is measured against a voltage drop.

Other methods of evaluating corrosion include (1) measurement of pit depth versus time and (2) visual interpretation of the percent of the corroded surface. The methods for evaluating corrosion heretofore used but do not actually measure corrosion or corrosion rate under controlled conditions of both the water film heat transfer coefficient as a function of velocity-caused shear effect, and surface temperature as a function of accurately controlled heat flux.

OBJECTS OF THE PRESENT INVENTION

An object of the present invention is to provide novel process and apparatus for measuring the corrosion rate of a heat transfer surface to a fluid.

Another object of the present invention is to provide novel process and apparatus for facile connection to an on-line unit or process heat exchanger for in-situ measuring of the corrosive rate of a heat transfer surface to a heat transfer fluid.

Still another object of the present invention is to provide a novel process and apparatus for facile connection to an on-line unit or process heat exchanger for in-situ measuring of the corrosive rate of a heat transfer surface to a heat transfer fluid.

SUMMARY OF THE INVENTION

These and other objects of the present invention are achieved by a fouling and corrosion test assembly including a metallic tube having a heating element embedded in a heat conductive material for controlled heat input and with a thermocouple to measure wall temperature of the tube, and a metallic sleeve disposed about a predetermined portion of the metallic tube whereby the fouling and corrosion test assembly is disposed within conduit and valve assemblies in fluid flow communication with a fluid to determine corrosion rate by weight loss of the metallic sleeve under controlled heat input, temperature conditions and fluid flow rates for a predetermined time period.

BRIEF DESCRIPTION OF THE DRAWINGS

Further objects and advantages of the present invention will become apparent upon consideration of the detailed disclosure thereof, especially when taken with the accompanying drawing wherein like numerals designate like parts throughout and wherein.

DETAILED DESCRIPTION OF THE DRAWINGS

Figure 1:
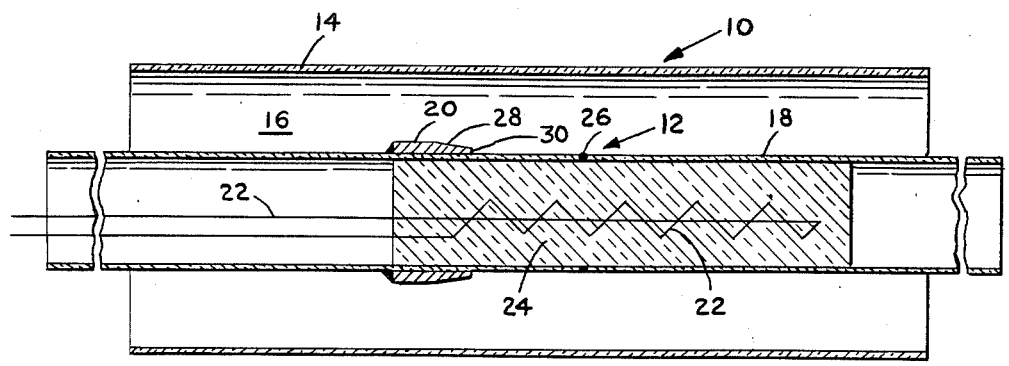
FIG. 1 is a cross-sectional elevational view of the present invention.
Figure 2:
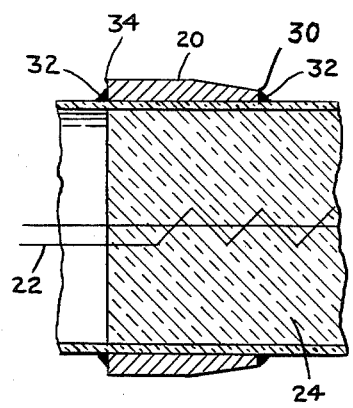
FIG. 2 is an enlarged cross-sectional view of a portion of FIG. 1 of the present invention.

Referring now to FIGS. 1 and 2, there is illustrated a test module, generally indicated as 10, comprised of a fouling and corrosion test assembly, generally indicated as 12 co-axially disposed within a conduit 14 forming an annular fluid flow passageway 16. The fouling and corrosion test assembly 12 is comprised of a cylindrically-shaped heating member 18 on which is positioned a cylindrically-shaped corrosion test sleeve member 20. The interior of the cylindrically-shaped heating member 18 is provided with a high resistant heating element 22 embedded within an insulating matrix 24, such as magnesium oxide, and with at least one thermocouple 26 embedded within the heating member 18 for sensing wall temperature.

The conduit 14 is preferably formed of any suitable transparent material, such as glass, to permit visual observation of fluid flow as well as any scale formation (not shown) about the surface of the heating member 18. The heating member 18 is formed of a metallic material, such as stainless steel, copper, titanium, mild steel, admiralty metal or the like, dependent, for example, on the tube material of a heat exchanger being evaluated, the fluid to be tested by passage through the test module 10, or of like metallic material to that in the unit through which the fluid to be tested is flowing. Generally, stainless steel is used for normal cooling water application, whereas admiralty metal is employed for sea water and brackish water applications.

The cylindrically-shaped corrosion test sleeve member 20 is generally formed of like material as that of the heating member 18 to duplicate the actual material of the heat transfer unit, as well as to eliminate corrosive effect of dissimilar metals. The test sleeve member 20 is of a minimum thickness to minimize heat transfer resistance yet permitting for high pitting type corrosion, a thickness of at least about 0.03 inches. To minimize the effect of eddy current on the surface of the test sleeve member 20, a leading surface portion 28 of the sleeve member is machined down to a leading edge 30 of a thickness of less than about 0.015 inches.

Figure 3:
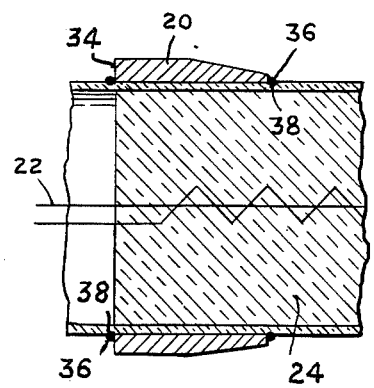
FIG. 3 is an enlarged cross-sectional view of a another embodiment of the present invention.

The test sleeve member 20 is preferably positioned, such as by spot welds of silver solders, on the heating member 18 with a trailing edge 34 thereof corresponding to the terminal portion of the insulating matrix 24 to minimize any water film upset at the thermocouple site. Alternately, the test sleeve member 20 may be positioned on the heating member 18 and held in place by O-rings of a resilient material 36 disposed in grooves 38 formed in the heating member 18, as shown in FIG. 3. To provide for simulation to like surface temperatures, the test sleeve member 20 is closely fitted, e.g. press fit, on the heating member 18, to provide for intimate contact therebetween and minimize any heat transfer resistance due to air entrapment.

The corrosive rate of a fluid is evaluated by weight loss to the test sleeve member 20 evidenced during the passage of the fluid through the test module 10 under controlled rates of flow and heat output from the heating element 18 per unit of time, as more fully hereinafter discussed.

Figure 4:
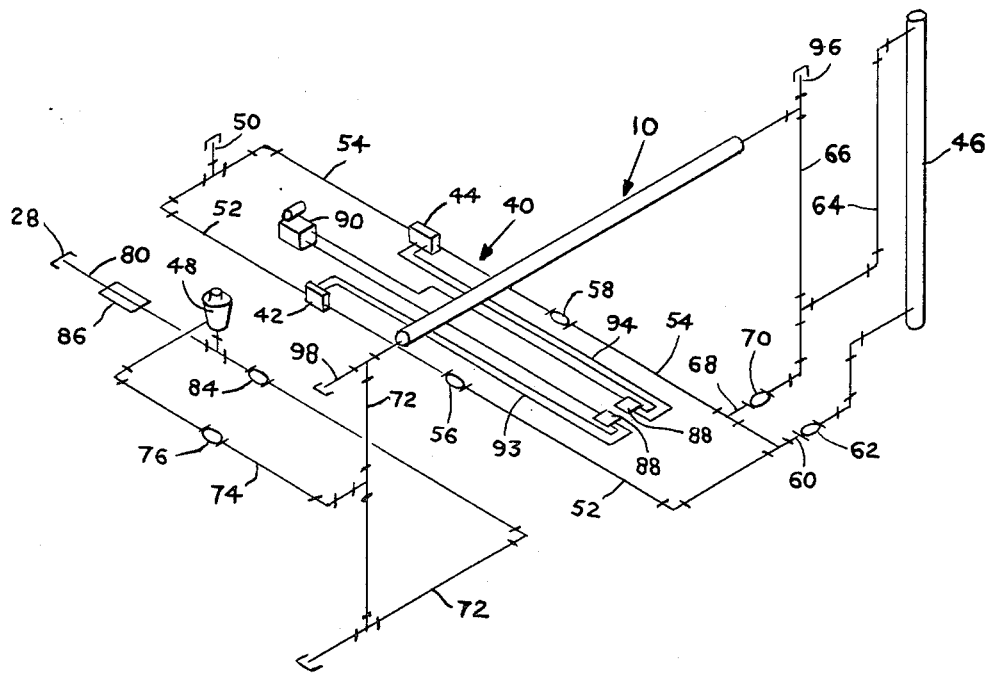
FIG. 4 is a piping diagram incorporating the apparatus of the present invention.

The heat test module 10 is positioned within a piping assemby, generally indicated as 40 referring now to FIG. 4, and includes flow meters 42 and 44, a rotameter 46 and a flow rate control valve 48. The piping assembly 40 is provided with an inlet conduit 50, in parallel flow communication with the flow meters 42 and 44 by conduits 52 and 54 under the control of valves 56 and 58, respectively. Conduits 52 and 54 are in fluid flow communication by conduit 60 under the control of an isolation valve 62 with one end of the rotameter 46 with the other end of the rotameter 46 being in fluid flow communication by conduits 64 and 66 with the inlet end of the test module 10. Conduit 54 is in fluid flow communication by conduit 68 under the control of by-pass valve 70 with conduit 66.

The outlet of the test module 10 is in fluid flow communication by conduit 72 and conduit 74 under the control of an isolation valve 76 via the flow rate control valve 48 to outlet 78 by conduit 80. Conduit 72 is in fluid flow communication with conduit 80 by conduit 82 under the control of a by-pass valve 84. The conduit 80 is provided with flow cell 86 including a plurality of probes (not shown) to measure other parameters of the fluid, as more fully hereinafter discussed.

The flow meters 42 and 44 are preferably of the venturi type with each meter having a different design rating of flow rates and are electrically connected via transducers 88 to a differential pressure cell 90 and by lead lines 92 and 94, respectively, which senses the pressure drop across the flow meters 42 and 44. The piping assembly 30 is provided with a thermocouple 96 to monitor the bulk inlet water temperature and with a high temperature cutoff 88.

In order to provide sufficient range of flow velocities, a plurality of test modules 10 of differing diameter may be used for interchangeable insertion into the piping assembly 40. The flow rate control valve 48 is preferably of the constant flow type with an internal pressure equalizer (not shown) to insure flow at the preselect valve. The rotameter 46 permit visual monitoring and may be electronically-monitored by a differential pressure cell (not shown).

The piping assembly 40 is integrated or coupled with a monitoring and recording assembly (not shown), as disclosed in the aforementioned copending applications, and mounted on a support structure for positioning within a mobile container, such as a trailer, van or the like, for facile movement from location to location to test a fluid passing through a unit, such as a heat exchanger, reactor or the like.

In operation, the monitoring and recording assembly including piping assembly disposed on a suitable support assembly and enclosed in a self-contained environmental container is caused to be positioned adjacent a unit operation or unit process, such as a heat exchanger or delignification digester, respectively, employing a fluid to be tested, inter alia, for the corrosive effect thereof to determine corrosion rate thereof to a heat transfer surface. A test module 10 is positioned within the piping assembly 40 including a heating member 18 and test sleeve member 20 formed of like material to that of the tubular members of the unit operation or process, with the test sleeve member 20 being weighed prior to positioning on the heating member 18. Once is place, the fluid to be tested is caused to be passed through the passageway 16 of the test module 10 Power is supplied to the heater element 22 of the heating member 18 and the temperature of the wall of the heating member 18 is monitored to obtain the temperature thereof. Simultaneously, the bulk fluid temperature is monitored by thermocouple 96 together with the monitoring of the fluid velocity. Water velocity is controlled by the constant flow valve 48 and is visually monitored by the rotameter 46 concomitant with electronic monitoring by the differential pressure cell 90 sensing the pressure drop across either flow meter 42 or 44.

After a predetermined time period e.g. from 7 to 30 days, with a minimum period of 2 to 3 days; fluid flow through the test module 10 is discontinued and the tests module 10 removed from the piping assembly 40. The test sleeve member 20 is removed from the heating member 18 and is weighed to permit calculation of weight loss to be incorporated into the following equation for calculating corrosion rate (CR):

$$CR = \frac{W_1 \cdot 365 \text{ days/year} \cdot 1000 \text{ mils/\delta in}}{16.39 \text{ cm } 3/\text{in}^3 \cdot A \cdot d \cdot t}$$

wherein,
$W_1$ is weight loss in grams,
A is the surface area of the sleeve in inches,
d is density of metal in grams per cc, and
t is test period in days.

While the present invention has been described in connection with an exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalent thereof.

What is claimed:
1. An apparatus for determining the corrosion rate of a fluid to a material, which comprises:

a heat transfer assembly to be disposed within a conduit of a piping assembly and including a cylindrically-shaped member having a heating element; and a pre-weighed metallic sleeve member press fitted about said cylindrically-shaped member, said metallic sleeve member and said cylindrically-shaped member being formed of like metal.

2. The apparatus as defined in claim 1 wherein said metallic sleeve member is of a thickness of at least about 0.03 inches.

3. The apparatus as defined in claim 1 wherein said metallic sleeve member is formed with a conically-shaped leading surface.

4. The apparatus as defined in claim 3 wherein a leading edge of said conically-shaped leading surface is of a thickness of at least 0.01 inches.

5. The apparatus as defined in claim 1 wherein said sleeve member includes a trailing edge coincident with an end portion of said heating element.

6. The apparatus as defined in claim 1 wherein said sleeve member is soldered to said cylindrically-shaped member.

7. The apparatus as defined in claim 1 wherein said cylindrically-shaped member is provided with circumferentially-formed grooves spaced apart a distance slightly greater than said sleeve member and further comprising O-ring member of resilient material disposed in said grooves for retaining said sleeve member on said cylindrically-shaped member.

8. The apparatus as defined in claim 1 wherein said heating element includes a high resistant heating element embedded in an insulating matrix.

9. The apparatus as defined in claim 1 wherein a thermocouple is embedded in said cylindrically-shaped member.

10. A process for determining a corrosion rate of a fluid to a heat transfer material utilizing a heat transfer assembly including a cylindrically-shaped member having an internal heating assembly, which comprises:

(a) positioning a pre-weighed cylindrically-shaped sleeve member about said heat transfer assembly, said internal heating assembly including an end porition, said cylindrically-shaped sleeve member being positioned at a downstream portion of said cylindrically-shaped member proximate said end portion of said internal heating assembly;

(b) placing said heat transfer assembly in a conduit in fluid flow communication with said fluid;

(c) energizing said internal heating assembly;

(d) monitoring and controlling electrical input to said internal heating assembly in response to a thermocouple mounted in said cylindrically-shaped member;

(e) discontinuing after a predetermined time period said flow of said fluid; and (f) removing and weighing said cylindrically-shaped sleeve member to determine weight loss during said predetermined time period.

11. The process as defined in claim 10 wherein said heat transfer assembly and said sleeve member are of like metal.

12. The process as defined in claim 10 wherein temperature of said heat transfer assembly is monitored.

13. The process as defined in claim 12 wherein step (c) is controlled in response to monitored temperature of said heat transfer assembly.

14. The process as defined in claim 10 wherein said internal heating assembly includes a high resistant heating element embedded in an insulated matrix.

15. The process as defined in claim 10 wherein a thermocouple is embedded in said cylindrically-shaped member.

16. The process as defined in claim 15 wherein said thermocouple mounted in said cylindrically-shaped member is for monitoring and controlling electrical input to said heating element.

* * * * *